(12) United States Patent
White et al.

(10) Patent No.: US 11,110,245 B2
(45) Date of Patent: Sep. 7, 2021

(54) BREATHING ASSISTANCE APPARATUS

(71) Applicant: Fisher & Paykel Healthcare Limited, Auckland (NZ)

(72) Inventors: Craig Karl White, Auckland (NZ); Jason Peter Van Beurden, Auckland (NZ); Kevin Peter O'Donnell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 205 days.

(21) Appl. No.: 16/432,672

(22) Filed: Jun. 5, 2019

(65) Prior Publication Data
US 2019/0366028 A1 Dec. 5, 2019

Related U.S. Application Data

(63) Continuation of application No. 14/500,482, filed on Sep. 29, 2014, now Pat. No. 10,350,376, which is a
(Continued)

(30) Foreign Application Priority Data

May 30, 2003 (NZ) ........................................ 526362

(51) Int. Cl.
*A61M 16/00* (2006.01)
*A61M 16/08* (2006.01)
(Continued)

(52) U.S. Cl.
CPC .... *A61M 16/0875* (2013.01); *A61M 16/0003* (2014.02); *A61M 16/0057* (2013.01);
(Continued)

(58) Field of Classification Search
CPC .......... A61M 16/0875; A61M 16/0003; A61M 16/0415; A61M 16/0622; A61M 16/0672;
(Continued)

(56) References Cited

U.S. PATENT DOCUMENTS

| 928,237 A | 7/1909 | Baird |
|---|---|---|
| 2,868,199 A | 1/1959 | Hudson |

(Continued)

FOREIGN PATENT DOCUMENTS

| AU | 200013529 | 6/2000 |
|---|---|---|
| CA | 2833707 | 11/2001 |

(Continued)

OTHER PUBLICATIONS

Canadian Exam Report for Application No. 3,018,256 dated Apr. 22, 2020, 4 pages.
(Continued)

*Primary Examiner* — Steven O Douglas
(74) *Attorney, Agent, or Firm* — Knobbe, Martens, Olson & Bear, LLP

(57) ABSTRACT

A nasal cannula assembly is disclosed having a face mount part, in use resting against a user's face, which includes at least one nasal prong capable of being fitted into a person's nares. The cannula assembly also includes a manifold part, in fluid communication with the face mount part, having a single horizontal side gases entry. In particular, this cannula assembly is for supplying heated, humidified gases to a patient suffering from COPD. A tie or lanyard is disclosed for use with a breathing assistance apparatus such as a nasal cannula, face or nasal mask or tracheostomy connector. The tie or lanyard transfers the weight of the conduits supplying gases to the breathing assistance apparatus from the breathing assistance apparatus and distributes it onto the neck of the patient.

22 Claims, 7 Drawing Sheets

Related U.S. Application Data continuation of application No. 13/592,069, filed on Aug. 22, 2012, now Pat. No. 8,851,076, which is a continuation of application No. 13/187,209, filed on Jul. 20, 2011, now Pat. No. 8,267,092, which is a continuation of application No. 12/389,017, filed on Feb. 19, 2009, now Pat. No. 8,220,463, which is a continuation of application No. 10/855,146, filed on May 27, 2004, now Pat. No. 7,493,902.

(51) Int. Cl.
  *A61M 16/10* (2006.01)
  *A61M 16/06* (2006.01)
  *A61M 16/16* (2006.01)
  *A61M 16/04* (2006.01)

(52) U.S. Cl.
  CPC ...... *A61M 16/0066* (2013.01); *A61M 16/024* (2017.08); *A61M 16/0415* (2014.02); *A61M 16/0622* (2014.02); *A61M 16/0666* (2013.01); *A61M 16/0672* (2014.02); *A61M 16/0683* (2013.01); *A61M 16/0688* (2014.02); *A61M 16/08* (2013.01); *A61M 16/0816* (2013.01); *A61M 16/109* (2014.02); *A61M 16/1095* (2014.02); *A61M 16/16* (2013.01); *A61M 2016/003* (2013.01); *A61M 2202/0208* (2013.01); *A61M 2205/3334* (2013.01); *A61M 2205/3368* (2013.01); *A61M 2205/52* (2013.01)

(58) Field of Classification Search
  CPC ............ A61M 16/0688; A61M 16/109; A61M 16/1095; A61M 16/024; A61M 16/0057; A61M 16/0066; A61M 16/0666; A61M 16/0683; A61M 16/08; A61M 16/0816; A61M 16/16; A61M 2016/003; A61M 2202/0208; A61M 2205/3334; A61M 2205/3368; A61M 2205/52
  See application file for complete search history.

(56) References Cited

U.S. PATENT DOCUMENTS

| | | |
|---|---|---|
| 3,144,313 A | 8/1964 | Pfefferie |
| 3,228,877 A | 1/1966 | Mahon |
| 3,245,206 A | 4/1966 | Bonnet |
| 3,292,346 A | 12/1966 | Adams |
| 3,303,105 A | 2/1967 | Konikoff et al. |
| 3,307,330 A | 3/1967 | Niedzielski et al. |
| 3,367,850 A | 2/1968 | Johnson |
| 3,376,181 A | 4/1968 | Larson et al. |
| 3,394,954 A | 7/1968 | Sarns |
| 3,434,471 A | 3/1969 | Liston |
| 3,513,844 A | 5/1970 | Smith |
| 3,578,777 A | 5/1971 | Degain |
| 3,616,796 A | 11/1971 | Jackson |
| 3,639,970 A | 2/1972 | Larkin |
| 3,682,171 A | 8/1972 | Dali et al. |
| 3,700,513 A | 10/1972 | Haberhauer et al. |
| 3,735,558 A | 5/1973 | Skarstrom et al. |
| 3,735,559 A | 5/1973 | Salemme |
| 3,754,552 A | 8/1973 | King |
| 3,803,810 A | 4/1974 | Rosenberg |
| 3,829,340 A | 8/1974 | Dembiak et al. |
| 3,856,051 A | 12/1974 | Bain |
| 3,871,373 A | 3/1975 | Jackson |
| 3,889,717 A | 6/1975 | Obadal et al. |
| 3,891,556 A | 6/1975 | Ricahrdson et al. |
| 3,895,630 A | 7/1975 | Bachman |
| 3,910,808 A | 10/1975 | Steward |
| 3,912,795 A | 10/1975 | Jackson |
| 3,963,856 A | 6/1976 | Carlson et al. |
| 3,966,525 A | 6/1976 | Steward |
| 4,007,737 A | 2/1977 | Paluch |
| 4,035,211 A | 7/1977 | Bill et al. |
| 4,048,993 A | 9/1977 | Dobritz |
| 4,083,245 A | 4/1978 | Osborn |
| 4,086,035 A | 4/1978 | Klaeger, Jr. et al. |
| 4,130,617 A | 12/1978 | Wallace |
| 4,204,562 A | 5/1980 | Kelly |
| 4,207,457 A | 6/1980 | Haglunc et al. |
| 4,216,769 A | 8/1980 | Grimes |
| 4,262,704 A | 4/1981 | Grawey |
| 4,265,235 A | 5/1981 | Fukunaga |
| 4,265,239 A | 5/1981 | Fischer, Jr. et al. |
| 4,318,398 A | 3/1982 | Oetjen et al. |
| 4,327,718 A | 5/1982 | Cronenberg |
| 4,327,775 A | 5/1982 | Tally |
| 4,336,798 A | 6/1982 | Beran |
| 4,337,800 A | 7/1982 | Carlson et al. |
| 4,343,672 A | 8/1982 | Kanao |
| 4,367,735 A | 1/1983 | Dali |
| 4,368,088 A | 1/1983 | Asakura et al. |
| 4,403,514 A | 9/1983 | Osborn |
| 4,406,283 A | 9/1983 | Bir |
| 4,406,514 A | 9/1983 | Hillegonds et al. |
| 4,417,574 A | 11/1983 | Talonn et al. |
| 4,420,016 A | 12/1983 | Nichols |
| 4,456,034 A | 6/1984 | Bixby |
| 4,462,397 A | 7/1984 | Suzuki |
| 4,463,755 A | 8/1984 | Suzuki |
| 4,469,495 A | 9/1984 | Hiraizumi et al. |
| 4,490,575 A | 12/1984 | Kutnyak |
| 4,493,870 A | 1/1985 | Vrouenraets et al. |
| 4,509,359 A | 4/1985 | Gedeon et al. |
| 4,580,816 A | 4/1986 | Campbell et al. |
| 4,592,351 A | 6/1986 | Smith et al. |
| 4,597,596 A | 7/1986 | Tozer |
| 4,621,632 A | 11/1986 | Bartels et al. |
| 4,653,542 A | 3/1987 | Tascher |
| 4,682,010 A | 7/1987 | Drapeau et al. |
| 4,686,354 A | 8/1987 | Makin |
| 4,698,196 A | 10/1987 | Fabian |
| 4,698,890 A | 10/1987 | Neaves |
| 4,705,543 A | 11/1987 | Kertzman |
| 4,708,831 A | 11/1987 | Elsworth et al. |
| 4,715,915 A | 12/1987 | Vanderzee |
| 4,722,334 A | 2/1988 | Blackmer et al. |
| 4,753,233 A | 6/1988 | Grimes |
| 4,771,770 A | 9/1988 | Artemenko et al. |
| 4,773,410 A | 9/1988 | Blackmer et al. |
| 4,791,963 A | 12/1988 | Gronert et al. |
| 4,808,201 A | 2/1989 | Kertzman |
| 4,825,863 A | 5/1989 | Dittmar et al. |
| 4,844,719 A | 7/1989 | Toyomoto et al. |
| 4,875,908 A | 10/1989 | Kikukawa et al. |
| 4,886,528 A | 12/1989 | Aaltonen et al. |
| 4,910,384 A | 3/1990 | Silver |
| 4,915,104 A | 4/1990 | Marcy |
| 4,915,105 A | 4/1990 | Lee |
| 4,919,128 A | 4/1990 | Kopala et al. |
| 4,932,269 A | 6/1990 | Cammarata, III et al. |
| 4,938,752 A | 7/1990 | Vrouenraets et al. |
| 4,967,744 A | 11/1990 | Chua |
| 4,985,055 A | 1/1991 | Thorne et al. |
| 4,995,384 A | 2/1991 | Keeling |
| 5,042,500 A | 8/1991 | Norlien et al. |
| 5,044,361 A | 9/1991 | Werner et al. |
| 5,046,531 A | 9/1991 | Kanao |
| 5,088,332 A | 2/1992 | Merilainen et al. |
| 5,160,511 A | 11/1992 | Lovelock |
| 5,165,395 A | 11/1992 | Ricci |
| 5,223,996 A | 6/1993 | Read et al. |
| 5,230,119 A | 7/1993 | Woods et al. |
| 5,233,996 A | 8/1993 | Coleman et al. |
| 5,273,032 A | 12/1993 | Borody |
| 5,284,160 A | 2/1994 | Dryden |
| 5,308,337 A | 5/1994 | Bingisser |
| 5,335,656 A | 8/1994 | Bowe et al. |
| 5,341,206 A | 8/1994 | Pittaro et al. |

(56) References Cited

U.S. PATENT DOCUMENTS

| | | | |
|---|---|---|---|
| 5,357,948 A | 10/1994 | Eilentropp |
| 5,365,938 A | 11/1994 | Eskela |
| 5,367,604 A | 11/1994 | Murray |
| 5,377,670 A | 1/1995 | Smith |
| 5,392,770 A | 2/1995 | Clawson et al. |
| 5,411,474 A | 5/1995 | Ott et al. |
| 5,427,291 A | 6/1995 | Smith |
| 5,438,978 A | 8/1995 | Hardester, III |
| 5,445,874 A | 8/1995 | Shehata |
| 5,445,875 A | 8/1995 | Persson |
| 5,454,061 A | 9/1995 | Carlson |
| 5,461,122 A | 10/1995 | Yilgor et al. |
| 5,462,048 A | 10/1995 | Lambert et al. |
| 5,501,212 A | 3/1996 | Psaros |
| 5,513,634 A | 5/1996 | Jackson |
| 5,532,053 A | 7/1996 | Mueller |
| 5,537,996 A | 7/1996 | Mcphee |
| 5,558,087 A | 9/1996 | Psaros et al. |
| 5,586,551 A | 12/1996 | Hillard |
| 5,595,174 A | 1/1997 | Gwaltney |
| 5,599,610 A | 2/1997 | Levy |
| 5,603,991 A | 2/1997 | Kupiecki et al. |
| 5,611,332 A | 3/1997 | Bono |
| 5,614,588 A | 3/1997 | Steenblock et al. |
| 5,620,500 A | 4/1997 | Fukui et al. |
| 5,623,922 A | 4/1997 | Smith |
| 5,630,409 A | 5/1997 | Bono et al. |
| 5,637,168 A | 6/1997 | Carlson |
| 5,640,951 A | 6/1997 | Huddart et al. |
| 5,645,054 A | 7/1997 | Cotner et al. |
| 5,653,228 A | 8/1997 | Bryd |
| 5,704,344 A | 1/1998 | Cole |
| 5,709,762 A | 1/1998 | Rowan |
| 5,715,647 A | 2/1998 | Keim et al. |
| 5,738,808 A | 4/1998 | Iwamoto |
| 5,769,071 A | 6/1998 | Tumbull |
| 5,794,619 A | 8/1998 | Edelman et al. |
| 5,794,986 A | 8/1998 | Gansel et al. |
| 5,798,013 A | 8/1998 | Brandenburger |
| 5,823,184 A | 10/1998 | Gross |
| 5,848,223 A | 12/1998 | Carlson |
| 5,850,833 A | 12/1998 | Kotliar |
| 5,862,651 A | 1/1999 | Stewart et al. |
| 5,862,652 A | 1/1999 | Schoeler |
| 5,894,839 A | 4/1999 | Rosenkoetter et al. |
| 5,964,219 A | 10/1999 | Pekka |
| 5,975,144 A | 11/1999 | Akedo et al. |
| 5,983,896 A | 11/1999 | Fukunaga et al. |
| 5,992,413 A | 11/1999 | Martin, Jr. et al. |
| 6,029,660 A | 2/2000 | Calluaud et al. |
| 6,033,368 A | 3/2000 | Gaston, IV et al. |
| 6,039,696 A | 3/2000 | Bell |
| 6,050,260 A | 4/2000 | Daniell et al. |
| 6,078,730 A | 6/2000 | Huddart et al. |
| 6,098,615 A | 8/2000 | Lloyd et al. |
| 6,105,576 A | 8/2000 | Clawson et al. |
| 6,116,235 A | 9/2000 | Walters et al. |
| 6,119,694 A | 9/2000 | Correa |
| 6,148,818 A | 11/2000 | Pagan |
| 6,167,883 B1 | 1/2001 | Beran et al. |
| 6,192,886 B1 | 2/2001 | Rudolph |
| 6,192,941 B1 | 2/2001 | Mallen-Herrero et al. |
| 6,201,223 B1 | 3/2001 | Nitta |
| 6,272,933 B1 | 8/2001 | Gradon et al. |
| 6,349,722 B1 | 2/2002 | Gradon et al. |
| 6,363,930 B1 | 3/2002 | Clawson et al. |
| 6,367,472 B1 | 4/2002 | Koch |
| 6,367,510 B1 | 4/2002 | Carlson |
| 6,378,520 B1 | 4/2002 | Davenport |
| 6,394,145 B1 | 5/2002 | Bailly |
| 6,412,481 B1 | 7/2002 | Bienvenu et al. |
| 6,431,172 B1 | 8/2002 | Bordewick |
| 6,432,169 B1 | 8/2002 | Kluwe et al. |
| 6,474,335 B1 | 11/2002 | Lammers |
| 6,516,798 B1 | 2/2003 | Davies |
| 6,523,538 B1 | 2/2003 | Wikefeldt |
| 6,536,428 B1 | 3/2003 | Smith et al. |
| 6,536,436 B1 | 3/2003 | McGlothen |
| 6,539,937 B1 | 4/2003 | Havari |
| 6,561,219 B1 | 5/2003 | Apostolides |
| 6,584,972 B2 | 7/2003 | McPhee |
| 6,595,215 B2 | 7/2003 | Wood |
| 6,637,434 B2 | 10/2003 | Noble |
| 6,662,802 B2 | 12/2003 | Smith et al. |
| 6,667,592 B2 | 12/2003 | Jacobs et al. |
| 6,684,883 B1 | 2/2004 | Burns |
| 6,718,973 B2 | 4/2004 | Koch |
| 6,742,399 B2 | 6/2004 | Kunz et al. |
| 6,769,431 B2 | 8/2004 | Smith et al. |
| 6,769,432 B1 | 8/2004 | Keifer |
| 6,779,522 B2 | 8/2004 | Smith et al. |
| 6,807,967 B2 | 10/2004 | Wood |
| 6,986,353 B2 | 1/2006 | Wright |
| 7,140,366 B2 | 11/2006 | Smith et al. |
| 7,493,902 B2 | 2/2009 | White et al. |
| RE40,806 E | 6/2009 | Gradon et al. |
| 7,559,324 B2 | 7/2009 | Smith |
| 7,900,628 B2 | 3/2011 | Matula et al. |
| 7,905,232 B2 | 3/2011 | Olsen et al. |
| 7,958,891 B2 | 6/2011 | Smith et al. |
| 8,037,882 B2 | 10/2011 | Smith et al. |
| 8,220,463 B2 | 7/2012 | White et al. |
| 8,267,092 B2 | 9/2012 | White et al. |
| 8,851,076 B2 | 10/2014 | White et al. |
| 8,905,082 B2 | 12/2014 | Gray |
| 8,980,036 B2 | 3/2015 | Smith et al. |
| 9,067,035 B2 | 6/2015 | Ophir et al. |
| 9,802,020 B2 | 10/2017 | Smith et al. |
| 9,827,393 B2 | 11/2017 | Smith et al. |
| 9,849,262 B2 | 12/2017 | White et al. |
| 9,878,120 B2 | 1/2018 | White et al. |
| 10,159,814 B2 | 12/2018 | Smith |
| 10,220,175 B2 | 3/2019 | White et al. |
| 10,252,017 B2 | 4/2019 | Smith et al. |
| 10,286,174 B2 | 5/2019 | Smith et al. |
| 10,350,376 B2 | 7/2019 | White et al. |
| 2002/0002976 A1 | 1/2002 | Smith et al. |
| 2002/0046755 A1 | 4/2002 | De Voss |
| 2002/0055685 A1 | 5/2002 | Levitsky et al. |
| 2002/0059935 A1 | 5/2002 | Wood |
| 2002/0195104 A1 | 12/2002 | Fini et al. |
| 2003/0028139 A1 | 2/2003 | Inoue |
| 2003/0047185 A1 | 3/2003 | Olsen et al. |
| 2003/0062048 A1 | 4/2003 | Gradon et al. |
| 2003/0070680 A1 | 4/2003 | Smith et al. |
| 2003/0094178 A1 | 5/2003 | McAuley et al. |
| 2003/0213490 A1 | 11/2003 | Righetti |
| 2006/0162726 A1 | 7/2006 | Smith et al. |
| 2007/0235100 A1 | 10/2007 | Tomerlin et al. |
| 2008/0072986 A1 | 3/2008 | Burrowes et al. |
| 2009/0025724 A1 | 1/2009 | Herron, Jr. |
| 2009/0088656 A1 | 4/2009 | Levitsky et al. |
| 2009/0126817 A1 | 5/2009 | Gray |
| 2012/0090622 A1 | 4/2012 | Chang |
| 2013/0098360 A1 | 4/2013 | Hurmez et al. |
| 2014/0180157 A1 | 6/2014 | Levitsky et al. |
| 2015/0208953 A1 | 7/2015 | Levitsky et al. |
| 2015/0306333 A1 | 10/2015 | Armadio et al. |
| 2016/0045702 A1 | 2/2016 | Milne et al. |
| 2017/0296769 A1 | 10/2017 | Smith et al. |
| 2018/0071477 A1 | 3/2018 | Smith et al. |
| 2018/0133428 A1 | 5/2018 | Smith et al. |
| 2019/0201649 A1 | 7/2019 | Smith et al. |
| 2019/0224439 A1 | 7/2019 | Lopez Muedano et al. |

FOREIGN PATENT DOCUMENTS

| | | |
|---|---|---|
| CA | 2346628 | 7/2010 |
| CA | 2697142 | 2/2014 |
| DE | 28036 | 2/1984 |
| EP | 0535379 | 4/1993 |
| EP | 0557040 | 8/1993 |
| EP | 0567158 | 10/1993 |
| EP | 0621050 | 10/1994 |

(56) References Cited

FOREIGN PATENT DOCUMENTS

| | | |
|---|---|---|
| EP | 0815792 | 1/1998 |
| EP | 0935971 A2 | 8/1999 |
| EP | 1014527 | 6/2000 |
| EP | 1166814 | 1/2002 |
| EP | 0747078 B1 | 10/2002 |
| EP | 0885623 B1 | 11/2004 |
| EP | 1524937 | 4/2005 |
| EP | 1477200 | 10/2006 |
| EP | 1153627 | 11/2007 |
| EP | 1885460 | 2/2008 |
| EP | 1681071 | 2/2009 |
| EP | 2226341 | 9/2010 |
| EP | 2305336 | 4/2011 |
| EP | 2025359 | 9/2013 |
| EP | 2666795 | 11/2013 |
| FR | 2638361 | 5/1990 |
| GB | 9683 | 4/1909 |
| GB | 587163 | 4/1947 |
| GB | 1492459 | 11/1977 |
| GB | 2024100 | 1/1980 |
| GB | 2252515 | 12/1992 |
| GB | 2139110 | 11/1994 |
| GB | 2284356 A | 6/1995 |
| JP | S62-236724 | 10/1987 |
| JP | 03-168155 | 7/1991 |
| JP | H05-052378 | 3/1993 |
| JP | H06-023051 | 2/1994 |
| JP | H09-234247 | 9/1997 |
| JP | 10248935 | 9/1998 |
| JP | 11323899 A | 11/1999 |
| JP | 2000-24111 | 1/2000 |
| JP | 2000-24113 | 1/2000 |
| WO | WO 88/01903 | 3/1988 |
| WO | WO 95/16746 | 6/1995 |
| WO | WO 95/33163 | 12/1995 |
| WO | WO 97/18001 | 5/1997 |
| WO | WO 98/02199 | 1/1998 |
| WO | WO 98/41148 | 9/1998 |
| WO | WO 99/64077 | 12/1999 |
| WO | WO 00/48682 | 8/2000 |
| WO | WO 01/41854 | 6/2001 |
| WO | WO 01/49351 | 7/2001 |
| WO | WO 2006/120683 | 11/2006 |
| WO | WO 2012/077052 A1 | 6/2012 |

OTHER PUBLICATIONS

European Examination Report for European Patent Application 17202695.7 dated Oct. 4, 2019.
Painter, Chris J., "Waterproof, Breathable Fabric Laminates: A Perspective from Film to Market Place", Journal of Coated Fabrics, vol. 26, Oct. 1996, pp. 107-130.
International Search Report, PCT/NZ2017/050074; dated Oct. 24, 2017.
One page off the Perma Pure Inc. website of the product brochure #104 of the New PD TM-Series Gas Dryers.
Three pages off the SympaTex website of some of the most common questions that are asked and some technical data on the SympaTex membrane.
Australian Patent Application No. 200143823 Published on Nov. 15, 2001 entitled Components for Breathing Cirucuits; Inventors Smith, Baldwin, Powell and Millar.
European Search Report, dated Mar. 7, 2011; 3 pages.
Canadian Examination Report; dated Jun. 27, 2012; 2 pages.
Office Action dated Mar. 11, 2015 for Canadian Application No. 2833707.
Canadian Examination Report; dated Mar. 23, 2011, 3 pages.
Canadian Examination Report; dated Apr. 6, 2016 in 3 pages.
Extended European Search Report for Application No. 10182233.6, dated Oct. 20, 2015.
European Search Report,Application No. 17202695.7; dated Aug. 3, 2018.
International Preliminary Report on Patentability in PCT/NZ2017/050074 dated Dec. 11, 2018 in 13 pages.
May 3, 2019 Complaint for Patent Infringement Demand for Jury Trial, *Fisher & Paykel Healthcare Limited v. Flexicare Incorporated*, Case No. 8:19-CV-00835.
European Examination Report for European Patent Application 17202695.7 dated Aug. 19, 2020, 4 pages.
BS 6151:1992 (ISO 5367:1991), British Standard, Specification for Breathing tubes for use with anaesthetic apparatus and ventilators, in 12 pages.
Canadian Examination Report for Application No. 3,018,256 dated Jan. 19, 2021, 4 pages.
R.D. Farley and D.H. Franklin, "Development of a humidifier for patient ventilation using a semi-permeable tube to minimize system condensate," J. Biomed. Eng., vol. 14, Sep. 1992.
MR700, MR720, MR730 Manual, in 48 pages.
Perma Pure Bulletin 104, in 4 pages.
K. Dijkstra Stroeks, "Modeling the moisture vapour transmission rate through segmented block co-poly(ether-ester) based breathable films," Polymer, vol. 42, Issue 1, Jan. 2001, pp. 117-127.
Adams et al; Thermoplastic Polyether Ester Elastomers; Supplied by British Library; unknown date.
MBM-200 Deltatrac II Service Manual; Datex/Division of Instrumentarium Corp; Mar. 1, 1993.
Sparrow; Flow Serparation in a Diversging conical duct: Effect of Reynolds number and divergence angle; International Journal of Heat and Mass Transfer; Jun. 2009.
Gibson; Effect of Temperature on Water Vapor Transport Through Polymer Membrane Laminates; U.S. Army; Feb. 1999.
Gibson; Measurement of water vapor diffusion through laminated fabrics and membranes using a diode laser spectroscope; US Army; Jan. 1998.
Gibson; On the Flow of Water through Pipes and Passages having converging or Diverging Boundaries; Univ. College, Dundee; Oct. 10, 1909.
Gravenstein; Gas Monitoring in Clinical Practice; Butterworth-Heinemann; 1995.
Johnson-Schultze; Breathable TPE Films for Medical Applications; Medical Device & Diagnostic Industry Magazine; Jul. 1, 2000.
Smart Anesthesai Multi-Gas SAM/SAM-80 Module Field Service Manual; Marquette Medical Systems; Mar. 27, 1998.
Flow of Fluids through Valves, Fittings, and Pipe; Crano Co., 1999.
www.permapure.com; capture from archive.org; ME-Series Moisture Exchangers; Perma Pure; Mar. 3, 2001.
www.permapure.com; capture from archive.org; Medical Gas Dryers; Perma Pure; Oct. 17, 2000.
www.permapure.com capture from archive.org; Dryers, Sampling Systems; Perma Pure; Jan. 27, 1999.
Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 17 pages.
Exhibit A, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 34 pages.
Exhibit B, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 16 pages.
Exhibit C, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 31 pages.
Exhibit D, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 15 pages.
Exhibit E, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 16 pages.

(56) References Cited

OTHER PUBLICATIONS

Exhibit F, Fisher & Paykel Healthcare Limited's Disclosure of Asserted Claims and Infringement Contentions, *Fisher & Paykel Healthcare Limited* v. *Flexicare Incorporated,* Case No. 8:19-CV-00835JVS(DFMx), Aug. 19, 2019, in 34 pages.
Exhibit G, Fisher & Paykel Healthcare Limited's Disclosure of Asserted Claims and Infringement Contentions, *Fisher & Paykel Healthcare Limited* v. *Flexicare Incorporated,* Case No. 8:19-CV-00835JVS(DFMx), Aug. 19, 2019, in 24 pages.
Exhibit H, Fisher & Paykel Healthcare Limited's Disclosure of Asserted Claims and Infringement Contentions, *Fisher & Paykel Healthcare Limited* v. *Flexicare Incorporated,* Case No. 8:19-CV-00835JVS(DFMx), Aug. 19, 2019, in 27 pages.
Exhibit I, Fisher & Paykel Healthcare Limited's Disclosure of Asserted Claims and Infringement Contentions, *Fisher & Paykel Healthcare Limited* v. *Flexicare Incorporated,* Case No. 8:19-CV-00835JVS(DFMx), Aug. 19, 2019, in 34 pages.
Exhibit J, Fisher & Paykel Healthcare Limited's Disclosure of Asserted Claims and Infringement Contentions, *Fisher & Paykel Healthcare Limited* v. *Flexicare Incorporated,* Case No. 8:19-CV-00835JVS(DFMx), Aug. 19, 2019, in 29 pages.
Flexicare Incorporated's Patent L.R. 3-3 Invalidity Contentions, *Fisher & Paykel Healthcare Limited* v. *Flexicare Incorporated,* Case No. 8:19-CV-00835JVS(DFMx), Oct. 17, 2019, in 54 pages.

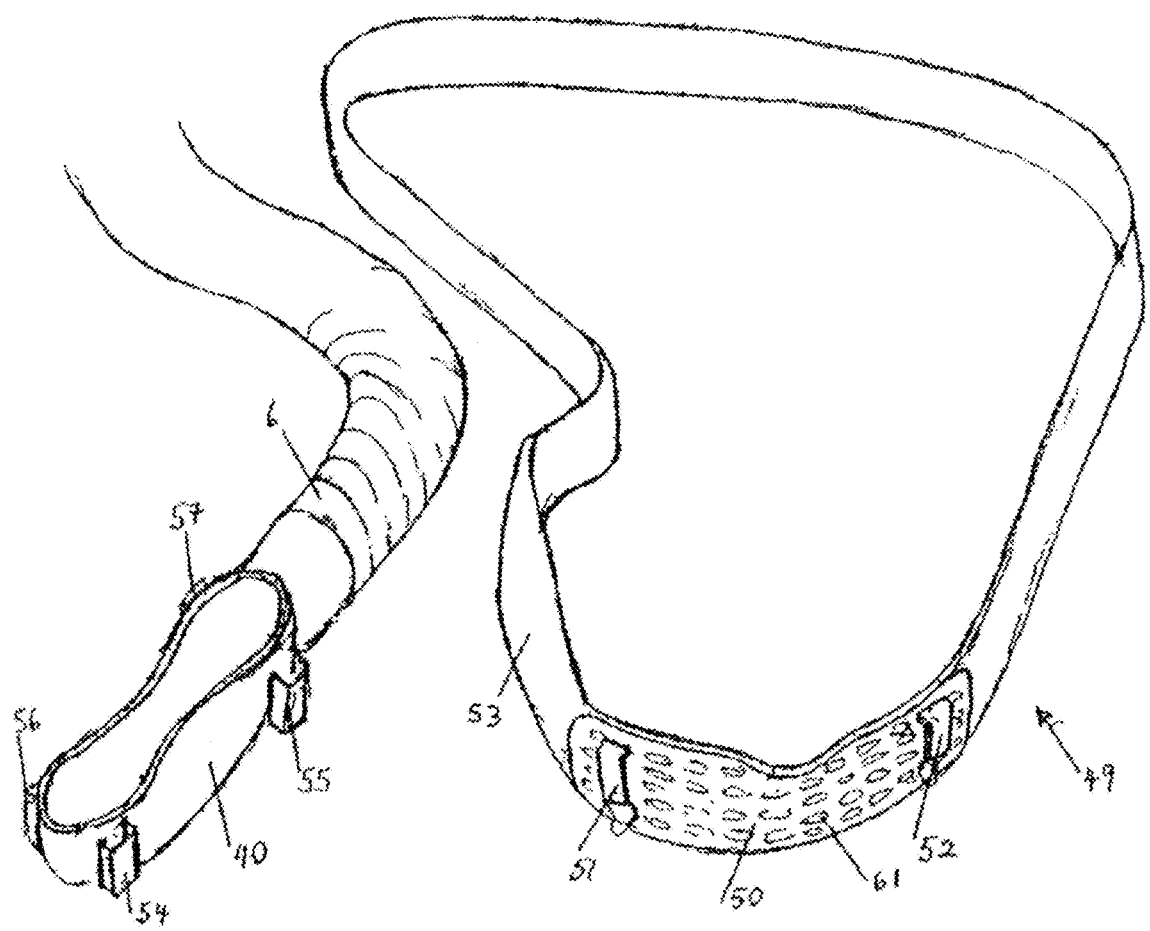
FIGURE 8
FIGURE 9
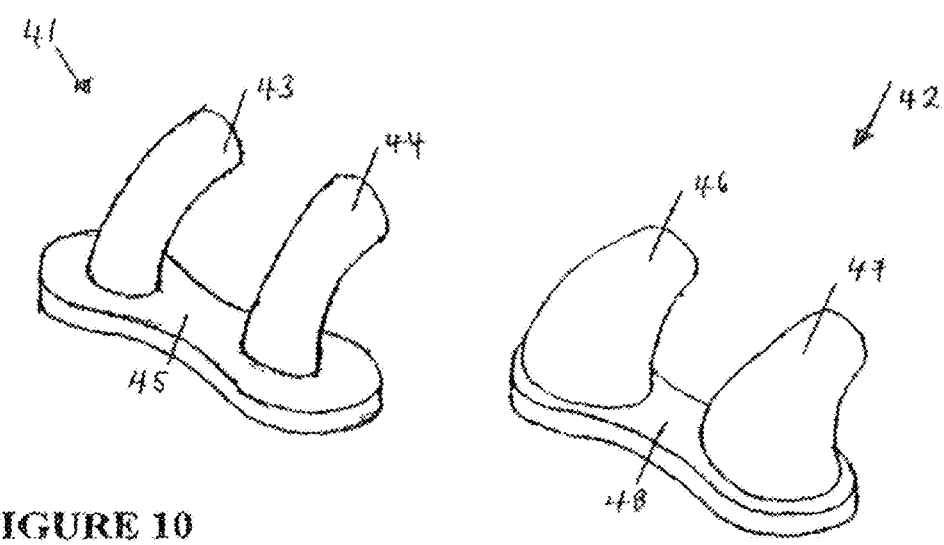
FIGURE 10
FIGURE 11

BREATHING ASSISTANCE APPARATUS

CROSS-REFERENCE TO RELATED APPLICATIONS

This application is a continuation of U.S. patent application Ser. No. 14/500,482, filed Sep. 29, 2014, which is a continuation of U.S. patent application Ser. No. 13/592,069, filed Aug. 22, 2012, and issued as U.S. Pat. No. 8,851,076, which is a continuation of U.S. patent application Ser. No. 13/187,209, filed Jul. 20, 2011, and issued as U.S. Pat. No. 8,267,092 on Sep. 18, 2012, which is a continuation of U.S. patent application Ser. No. 12/389,017, filed on Feb. 19, 2009, and issued as U.S. Pat. No. 8,220,463 on Jul. 17, 2012, which is a continuation of U.S. patent application Ser. No. 10/855,146, filed on May 27, 2004 and issued as U.S. Pat. No. 7,493,902 on Feb. 24, 2009, which claimed the priority benefit under 35 U.S.C. § 119 of New Zealand Patent Application No. 526,362, filed on May 30, 2003. Each of these applications is hereby incorporated by reference in its entirety.

BACKGROUND OF THE INVENTION

Field of the Invention

The present invention relates particularly, though not solely, to the delivery of high flow humidified pressurized oxygen and/or air to a patient in need of respiratory support by way of a nasal cannula

Description of the Related Art

Nasal cannula generally consist of entry tubing, either symmetric or single sided that lies across the upper lip. Protruding from this tubing are open ended prongs which extend into the nares of the patient to deliver oxygen. Nasal cannulae have the advantage of being more comfortable and acceptable than a facemask to most patients. The existing market for nasal cannula is well serviced by devices suitable for the delivery of gases in the 0 to 5 liter per minute range. These devices are typically supplied by a double entry lumen of small diameter (2-3 mm range) that supplies both sides of the nasal cannula and provides even airflow to each nasal prong. These devices work well for the delivery of low humidity gas flows of between 0 to 5 liter per minute and have been well received by patients over the last 30 years.

Hudson Respiratory Care Incorporated manufactures a nasal cannula that is disclosed in U.S. Pat. No. 2,868,199 that consists of a single flow entry nasal cannula. This single flow entry has the advantage of being unobtrusive, and more relevant to delivering humidity than a dual flow entry style of nasal cannula, simply due to the advantage of flow rates and surface area for heat loss. The single flow entry is on the left side only, which causes the user difficulty in use if the flow source is on the opposite side of the user requiring longer lengths of tubing and causing the tube to cross the body. The cannula itself is manufactured as one part only, of PVC plastic. This product is not designed for delivering high flow or high humidity gases. The nasal prongs are less than 3 mm in diameter resulting in noise and high velocity jetting of gas causing severe irritation at high flows. These cannulae are difficult to clean inside, are uncomfortable, and the prongs are too rigid for extended therapies.

U.S. Pat. No. 3,754,552 of Sandoz-Wander, Inc. discloses a nasal cannula, having two nasal prongs, adapted for the intake of therapeutic gas from either the right or left side of the patient. Here the nasal cannula has a bore within it that feeds each prong. The bore is able to receive a tube for supplying gases to the cannula in either end and in use a plug is required to obstruct the unused end.

Innomed Technologies, Inc. manufactures a nasal cannula device called the NASALAIRE™. This nasal cannula is a dual flow entry style cannula where two large tubes come from behind the ears, through the field of vision to the upper lip. In this device air or oxygen travels down a wide bore conduit to the nasal cannula. The NASALAIRE™ creates a physical seal between the nares and itself, and relies on the absence of leaks around itself and the nares to deliver pressure supplied by a continuous positive airway pressure (CPAP) blower to the airway of the wearer. The wearer is required to breathe in and out of the NASALAIRE™, thereby rebreathing some of the exhaled air from the lungs. The NASALAIRE™ is not designed to deliver humidified gases to the patient, being unheated and without insulation of any type. The NASALAIRE™ cannula is uncomfortable especially if a patient rests on the tube, as would happen during sleep, and is also obtrusive.

The new application of high airflow extended therapies using nasal cannulae generally result in the nasal cannula reaching temperatures in excess of 35 degrees C. Usually cannulae are made from soft polymeric material (for example, silicone) that absorbs heat and does not breathe and therefore sweat is generated under the contact points with the skin. This heat in combination with the polymeric materials waterproof properties results in sweat being trapped against a patient's skin and the patient has the sensation of overheating. The trapped sweat is uncomfortable and could lead to rashes.

Oxygen is generally supplied as a dry gas, but it is well known in the art to either heat and/or humidify gases before delivering them for breathing by a patient. In particular when delivering oxygen, or an oxygen air mixture, it has proven beneficial to humidify the gases first. In WO 01/41854 of Vapotherm, Inc. a system is disclosed that allows the delivery of humidified oxygen through a nasal cannula. This system uses a narrow bore conduit and nasal cannula with a high resistance to gas flows, thereby requiring the oxygen be of a high pressure. Air, as well as oxygen, can also be passed down the conduit and nasal cannula and it too must be of a high pressure. This system allows the delivery of high flows of oxygen enriched air to the patient, but is limited in the flows achievable due to the narrow bore of the cannula resulting in high resistance gas flow and excessive velocity and noise upon exiting the cannula. Furthermore, the narrowness of the nasal cannula in this system allows the patient to easily expire gases from their nostrils as there is a reasonable gap between the prongs and the patient's nares. Thus positive airway pressure is not created and as such this cannula is not suitable for the treatment of Obstructive Sleep Apnea (OSA).

In breathing circuits that supply respiratory gases to a patient by way of a patient interface, such as a nasal cannula, mask or tracheal tube, it is common to have a heated breathing circuit or tube delivering heated and humidified gases to the patient, followed by a short length of non-heated tube close to the patient. This unheated tube may be a short unheated extension tube or catheter mount. The unheated section of tube is usually intended to be very flexible to reduce torsion or pulling on the patient interface, to allow the gases to cool slightly towards the dew point of the gas, and also to eliminate hot surface temperatures near the patient. As this tube is unheated the temperature of the tube walls are colder than the dew point temperature of the gas, as a result the vapor in the gases passing near these walls will begin to condense out. Over time a build up of condensate close to the patient may lead to a build-up of bacteria which may cause infection. Build up of condensation may also create noise, such as gurgling, which may wake a patient, and in extreme circumstances the fluid build up may cause drowning.

When providing humidified gases to a patient it is common to use a heated breathing circuit (tubing). This circuit is heavy and can drag and pull on the patient interface. This is more pronounced if the patient is mobile and can be painful and/or dangerous if the patient interface is invasive such as an endotracheal tube. It is common to use a short flexible tube between the heated circuit and patient interface to reduce any torque or twisting. In order to stop the weight pulling on the patient interface, circuit hangers are occasionally used. This is a large extendable metal arm to take the weight. It also has been known in the art to clip part of the tubing to the patient's clothes or bedclothes. Both of these solutions have been found to be quite unsuitable for mobile patients especially when sleeping and turning in bed.

With patient interfaces such as nasal cannulae the stability of the nasal prongs on the face is very important, as movement of the prongs within the nares can cause severe irritation. Current methods employed to retain a single entry nasal cannula on the face use a simple elastic band of material around the back of the patients head. This is prone to rotating the nasal cannula relative to the patient's head especially when turning ones head on a pillow. This rotation causes the prongs move within the nares, irritating this sensitive area.

SUMMARY OF THE INVENTION

It is an object of the present invention to provide a breathing assistance apparatus which goes someway to overcoming the above mentioned disadvantages or which will at least provide the public a useful choice.

Accordingly in a first aspect the present invention consists in a nasal cannula assembly adapted to deliver gases to a patient comprising: a face mount part, including at least one nasal prong capable of being fitted into at least one of said patient's nares, a removable gases flow manifold part in use in fluid communication with said face mount part, said manifold part having a single horizontal side gases entry, in use, in fluid communication with said transport means.

In a second aspect the present invention may broadly be said to consist in a breathing assistance apparatus comprising: a pressurized source of gases, humidification means adapted to, in use, be in fluid communication with said source of gases and adapted to in use humidify said gases, humidified gases transport means adapted to, in use, be in fluid communication with said humidification means and adapted to in use convey said humidified gases, heating means disposed within said transport means and adapted to in use heat said gases as they pass through said transport means, and nasal cannula, adapted to deliver said humidified gases to said patient, said nasal cannula comprising a face mount part, including at least one nasal prong capable of being fitted into at least one of said patient's nares, a removable gases flow manifold part in use in fluid communication with said face mount part, said manifold part having a single horizontal side gases entry, in use, in fluid communication with said transport means.

The invention consists in the forgoing and also envisages constructions of which the following gives examples.

BRIEF DESCRIPTION OF THE DRAWINGS

Preferred forms of the present invention will now be described with reference to the accompanying drawings.

FIG. 8 is a perspective view of a third form of the nasal cannula assembly of the present invention, particularly showing a gases flow manifold part that allows for the attachment of removable prongs.

FIG. 9 is a perspective view of the third form of the nasal cannula assembly of the present invention, showing a strap and breathable pad fittable to the manifold part of FIG. 8.

FIG. 10 is a perspective view of a first form of removable prongs capable of being attached to the manifold part of FIG. 8.

FIG. 11 is a perspective view of a second form of removable prongs capable of being attached to the manifold part of FIG. 8.

DETAILED DESCRIPTION OF THE PREFERRED EMBODIMENT

Whether used in a hospital environment or in a home environment, the nasal cannula assembly of the present invention will generally have associated three main pieces of apparatus. Firstly an active humidifier that controls the temperature of a heater plate heating a body of water to achieve a desired temperature and humidity of the gases being humidified. Secondly a transport conduit from the humidifier to the patient is also required, which is preferably heated to reduce condensation, or "rain out". Thirdly a nasal cannula designed to fit into the nasal cavity of a patient or user and deliver humidified, pressurized gases.

Figure 1:
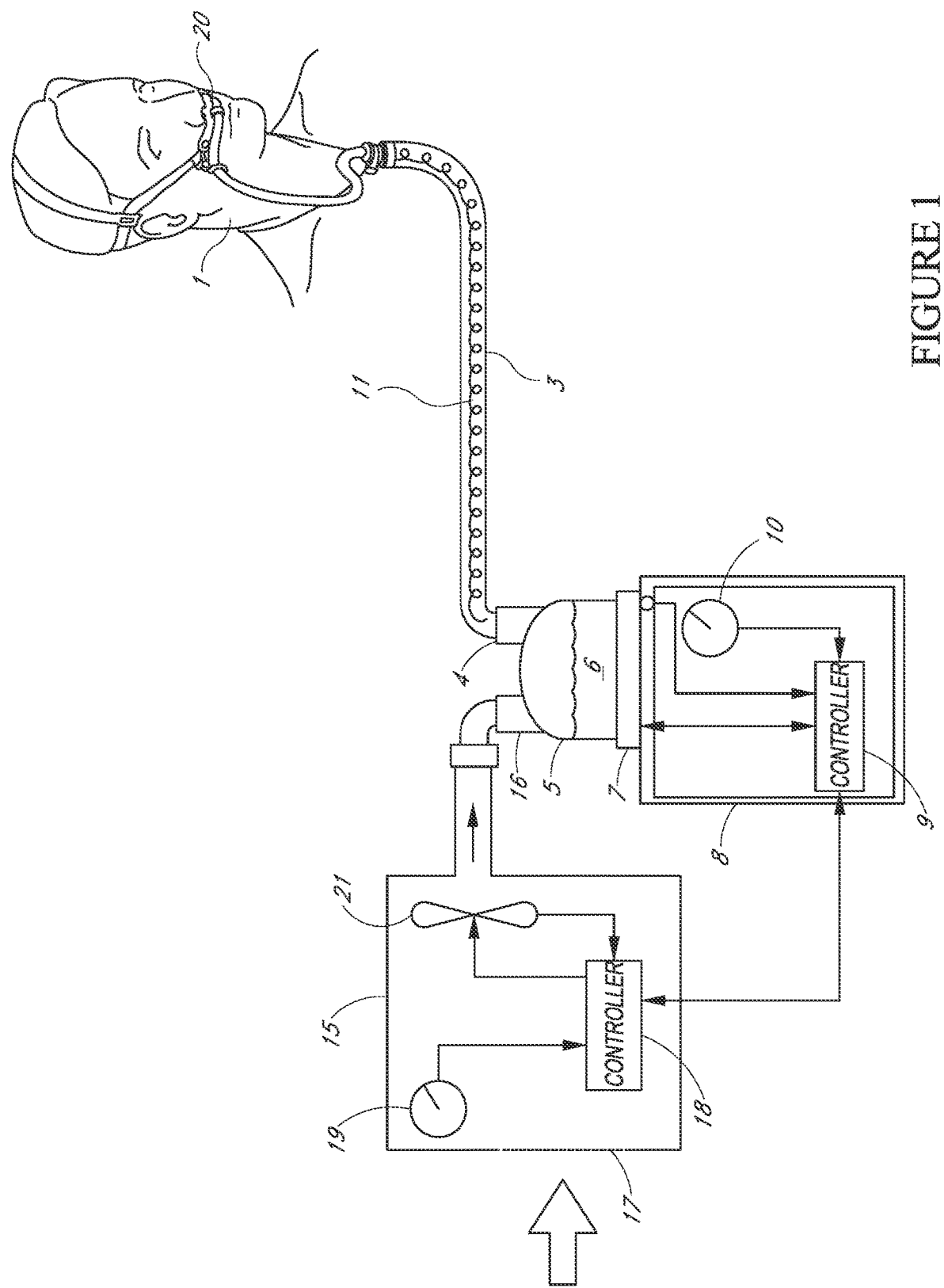
FIG. 1 is an illustration of a respiratory humidifier system that may be used with the nasal cannula assembly of the present invention.

Referring to FIG. 1 a humidifying circuit as might be used with the nasal cannula of the present invention is shown. A patient 1 is receiving humidified and pressurized gases through a nasal cannula 20 connected to a humidified gases transportation pathway or inspiratory conduit 3 that in turn is connected to a humidifier 8 (including humidification chamber 5) that is supplied with gases from a blower 15 or other appropriate gases supply means. The inspiratory conduit 3 is connected to the outlet 4 of a humidification chamber 5 which contains a volume of water 6. Humidification chamber 5 is preferably formed from a plastics material and may have a highly heat conductive base (for example an aluminium base) which is in direct contact with a heater plate 7 of humidifier 8. The humidifier 8 is provided with control means or electronic controller 9 which may comprise a microprocessor based controller executing computer software commands stored in associated memory. Gases flowing through the inspiratory conduit 3 are passed to the patient by way of the nasal cannula 20.

Controller 9 receives input from sources such as user input means or dial 10 through which a user of the device may, for example, set a predetermined required value (preset value) of humidity or temperature of the gases supplied to patient 1. In response to the user set humidity or temperature value input via dial 10 and other possible inputs such as internal sensors that sense gases flow or temperature, or by parameters calculated in the controller, controller 9 determines when (or to what level) to energize heater plate 7 to heat the water 6 within humidification chamber 5. As the volume of water 6 within humidification chamber 5 is heated, water vapor begins to fill the volume of the chamber above the water's surface and is passed out of the humidification chamber 5 outlet 4 with the flow of gases (for example air) provided from a gases supply means or blower 15 which enters the chamber through inlet 16. It should be noted that it is possible to obtain the relationship between the humidity of the gases in humidification chamber 5 and the temperature of the heater plate 7. Accordingly, it is possible to utilize the heater plate temperature in an algorithm or a look-up table to determine the humidity of the gases.

The blower 15 may be provided with a variable speed pump or fan 2 which draws air or other gases through the blower inlet 17. The speed of variable speed pump or fan 2 may be controlled by a further control means or electronic controller 18 (or alternatively the function of this controller 18 could be carried out by the other controller 9) in response to inputs from controller 9 and a user set predetermined required value (preset value) of pressure or fan speed via dial 19.

A heating element 11 may be provided within the conduit or tubing 3 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element is effectively replaces the energy lost from the gases through conduction and convection during transit through the conduit. Thus the conduit heater element ensures the gases delivered are at an optimal temperature and humidity.

Side Entry Nasal Cannula

The nasal cannula assembly of the present invention provides a patient with a patient interface suitable for the delivery of high airflow, high humidity gas flow to the patient's nasal cavity. A particular aspect of the nasal cannula of the present invention is the suitability for long term therapy where the patient, for example, a patient suffering from Chronic Obstructive Pulmonary Disease (COPD), will wear the cannula for several hours per day over weeks, months and in some cases years. Therefore, for patients to accept use of nasal cannula under these circumstances the cannula need to be unobtrusive, comfortable to wear, noise free, suitable for wearing while sleeping, easy to clean and have prongs that can generate Positive End Expiry Pressure (PEEP). The cannula of the present invention may also be used for other therapies such as for Continuous Positive Airway Pressure (CPAP) therapy and the like.

Figure 2:
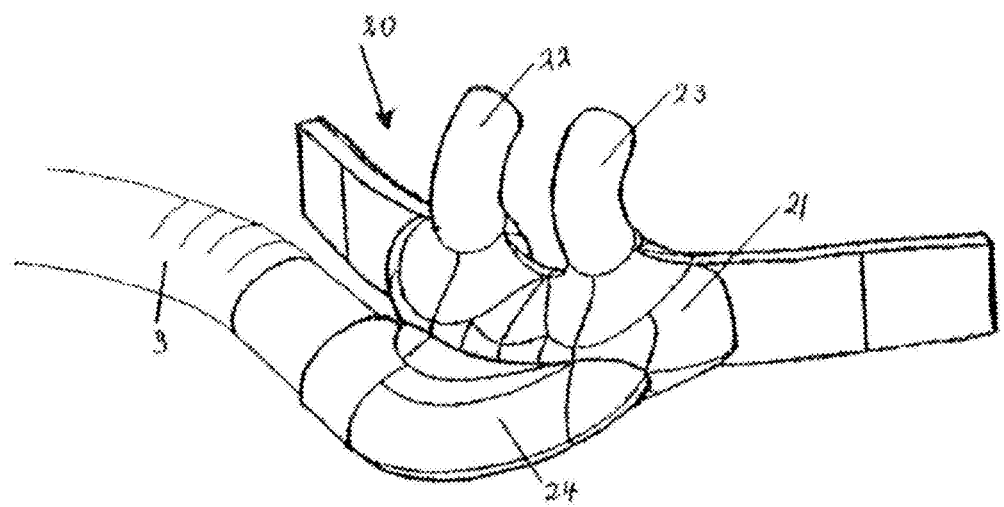
FIG. 2 is a perspective view of a first form of the nasal cannula assembly of the present invention.
Figure 3:
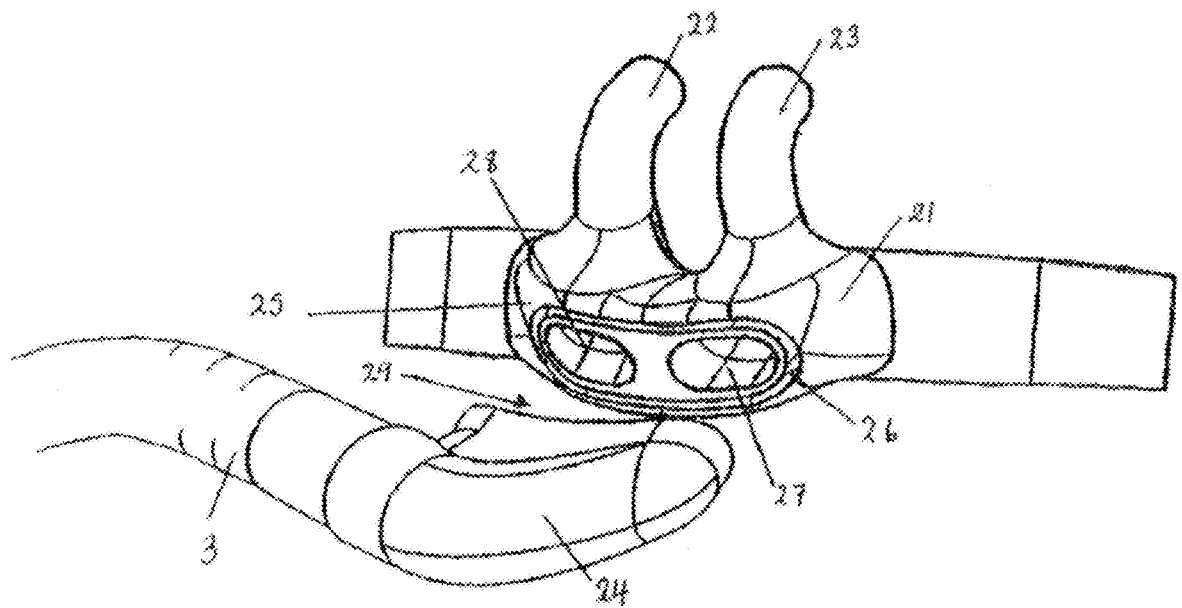
FIG. 3 is an exploded perspective view of the first form of the nasal cannula assembly of FIG. 2, showing two parts making up the nasal cannula, a face mount part and gases flow manifold part attached to tubing supplying gases to the patient.
Figure 4:
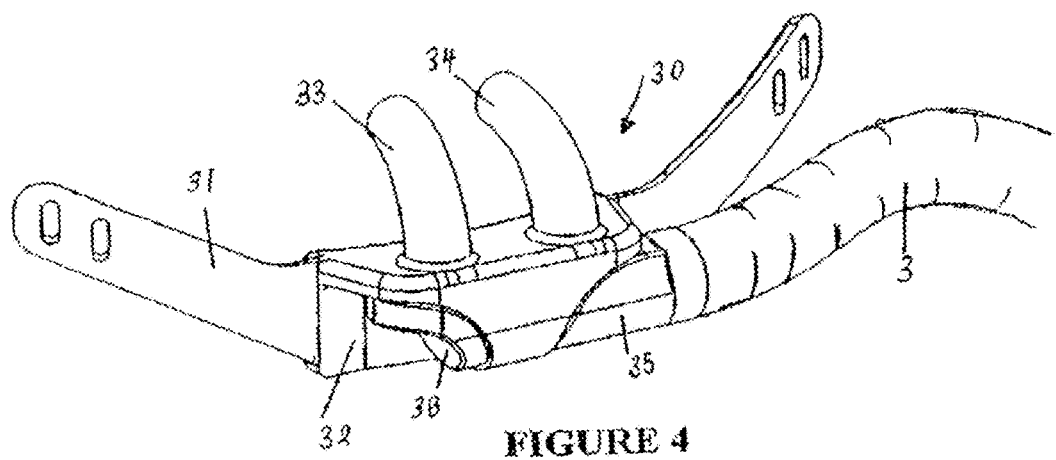
FIG. 4 is a perspective view of a second form of the nasal cannula assembly of the present invention, showing tubing providing a gases supply to a gases flow manifold part and face mount part when in connection.
Figure 5:
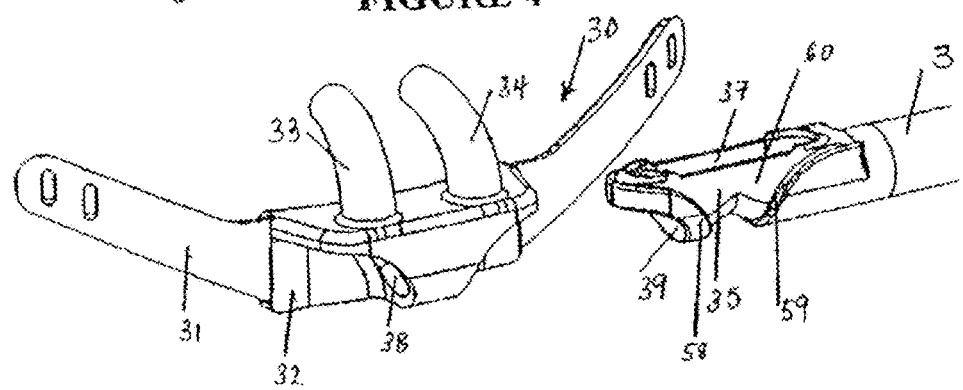
FIG. 5 is a perspective view of the second form of the nasal cannula assembly of FIG. 4 where the gases flow manifold part is disengaged from the face mount part.
Figure 6:
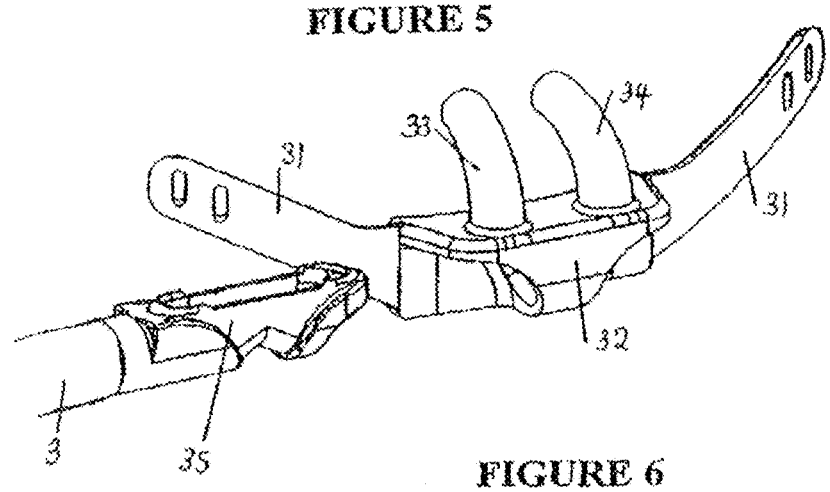
FIG. 6 is a perspective view of the second form of the nasal cannula assembly of FIG. 4 where the gases flow manifold part is disengaged from the face mount part, showing the manifold part can be fitted to either side of the face mount part.

A first form of the nasal cannula assembly of the present invention is shown in FIGS. 2 and 3. This nasal cannula, generally indicated as 20, comprises a face mount part 21 including a pair of tubular nasal prongs 22, 23 integrally molded with or removable attached to the face mount part 21, and a gases flow manifold part 24 that is integrally molded with or attached to tubing 3, such as that described above.

The face mount part 21 and prongs 22, 23 are preferably molded from silicone or other flexible material as is known is the art of cannula construction. The gases flow manifold part 24 is preferably made from a hard plastics material, although it may be manufactured in other suitable materials.

The face mount part 21 is preferably integrally molded with the prongs 22, 23 and is shaped to generally follow the contours of a patient's face around the upper lip area. The inner side (not shown) of the face mount part 21 may be provided with a breathable pad, to be described below. The outer side 25 of the face mount part 21 has molded in it an elongated oval recess 26 and two oval recesses 27, 28 that extend through the face mount part 21 and each meet the tubular passageways formed within each of the tubular prongs 22, 23.

The gases flow manifold part 24 is generally tubular in shape having a substantially circular inlet (not shown) on one side that curves around to an elongated oval outlet 29. The circular inlet receives the end of the conduit or tubing 3, so that gases are supplied to the gases flow manifold part 24 and are able to flow through the inlet and out the outlet 29. The tubing 3 is preferably permanently fixed to the manifold part 24, but may be releasably attachable.

The outlet 29, being elongated and oval in shape, fits into the elongated recess 26 in a friction or snap fit engagement with the manifold 21, such that a substantial force is required to remove the manifold part 24 from the elongated recess 26. Further, as the face mount part 21 is flexible and the manifold part 24 made from a harder plastics material it is possible for the manifold part outlet 29 to be easily pushed or forced into the elongated recess 26. When the manifold part 24 is engaged with the face mount part 21 and in use, gases flow from the tubing 3, through the gases flow manifold part 24 out its outlet 29, into each of the oval recesses 27, 28, into each of the prongs 22, 23 and into the patient's nares.

The face mount part elongate recess 26 and manifold part outlet 29 are symmetrical in shape and configuration and therefore the manifold part 24 is capable of being switched or flipped such that the tubing 3 extends from either the left or right side of the patient's nares. This means that the nasal cannula assembly 20 and associated tubing 3 are relatively unobtrusive as the cannula 20 only requires a single horizontal side entry, not two entries as that of the prior art.

The nasal cannula assembly of the present invention is more comfortable to wear as it sits under the septum of the nose and supports the two nasal prongs. As the prongs are made in one molding of a soft material such as silicone the prongs are easy to insert in the patient's nares and comfortable to the patient.

For a nasal cannula assembly to be suitable for wearing during sleep each night the cannula must be noise free. Many prior art cannulas are prone to whistling. With a range of airflows generally being between 0 to 40 liters per minute, although airflows of 60 liters per minute are envisaged for the present nasal cannula, and with the air or gases being supplied to a single horizontal entry point it has proved difficult to prevent whistling. For this reason the face mount part 21 is contoured such that the pressure distribution within the face mount part 21 forces even airflows up each nasal prong.

As the nasal cannula assembly of the present invention is likely to be used while a patient is sleeping, the cannula must be easily tailored for the patients sleeping arrangement. The cannula of the present invention supplies high flow humidified gases to the patient from either the left side or the right side of the cannula thus allowing the minimum length connection circuit to the bedside unit supplying the humidified gas. As the nasal cannula assembly of the present invention allows for the horizontal entry of gases from either side the patient can configure the unit as left or right entry for their particular sleeping arrangement. It is envisaged that the tubing 3 is approximately two meters in length to allow for added flexibility of the cannula.

Reference is now made to FIGS. 4 to 7 that show a second form of the nasal cannula assembly of the present invention. In this form the nasal cannula assembly 30 is of a substantially similar form to the first form described above in relation to FIGS. 2 and 3, and has a face mount part 32, a pair of nasal prongs 33, 34, gases flow manifold part 35 and tubing 3. The face mount part 32 and pair of nasal prongs 33, 34 are preferably integrally molded as one piece from a soft plastics material such as silicone, although in other forms the face mount part and prongs may be separate, but capable of attachment together for use.

The nasal prongs 33, 34 are tubular in shape and may be consistent in diameter but may be shaped to fit the contours of the human nares.

A strap or strap attachment means 31 may be integrally formed or attached to the face mount part 32 in order to enable the nasal cannula assembly 30 to be held in place about a patient's face.

The face mount part 32 has an open tubular recess 38 extending below the nasal prongs 33, 34 that is capable of receiving a gases flow manifold part 35 that is attached to or integrally formed with tubing 3. The tubular passageways within the nasal prongs 33, 34 extend through the face mount part and into the recess 38. The gases flow manifold part 35 is blocked at one end 39 but attached to the tubing at the other end and has an elongate opening 37 that acts as an exit for gases received from the tubing 3. Due to the flexible nature of the material the face mount part 32 is made from, and as the gases flow manifold part 35 is made from a hard plastics material, the gases flow manifold part 35 can be pushed through the tubular recess 38 in the face mount part 32 and the elongate opening 37 in the gases flow manifold part 35 meets with the tubular passageways of the prongs 33, 34. Therefore, in use, gases flowing through the tubing and into the gases flow manifold part 35 exit through the opening 37 and into the tubular passageways in the prongs 33, 34, then into the patient's nares.

In order to assist with maintaining the gases flow manifold part 35 within the manifold recess 38 the manifold part 35 is provided with an inner recessed portion 60 and contoured lip areas 58, 59. When engaged with the face mount part 32 the tubular body forming the recess 38 sits within the inner recessed portion 60 and the edges of the tubular body abut the lips 58, 59 formed on the manifold part 35.

Breathable Pad

Figure 7:
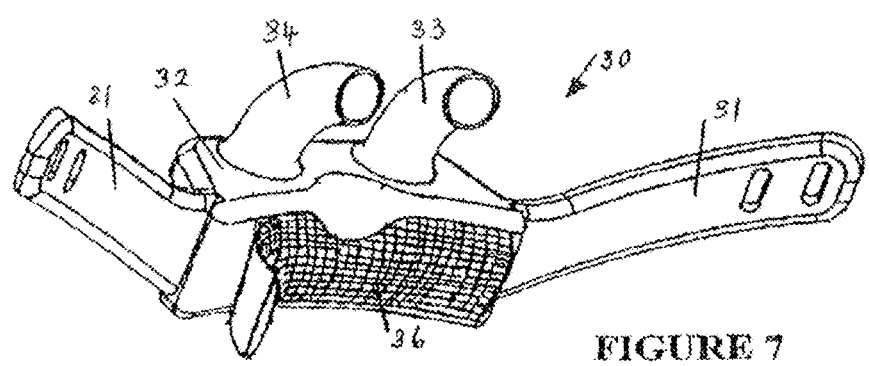
FIG. 7 is a back perspective view of the second form of the nasal cannula of FIG. 4, showing a removable breathable pad on the inner side of the face mount part that abuts the patients face.

A breathable pad may be supplied with any of the nasal cannula assemblies described above. In particular, such a pad 36 is shown in FIG. 7 in the second form of the nasal cannula assembly as described above. It must be appreciated that a pad of this type may be provided with any of the other two forms as herein described.

The pad is preferably attached to the inside surface of the face mount part 32 that connects with the upper lip of the patient wearing the cannula. The pad 36, which is preferably made from an absorbent cloth, reduces the incidence of heat and moisture on the patient's upper lip, where the face mount part 32 sits against their face.

The pad 36 is preferably attached to the face mount part 32 by adhesive, for example, the pad could be supplied with a sticky backing that adheres to the face mount part, so that the pad can be easily removed from the face mount part and replaced as necessary.

The pad reduces the effects of heat against the patient's skin and improves hygiene, as any contaminants or cultures that may grow close to the patient's skin, in the warm environment can be removed on removal and replacement of the pad.

Three Part Nasal Cannula

Referring now to FIGS. 8 to 11, a third form of the nasal cannula assembly of the present invention is shown where the nasal cannula assembly comprises three parts.

Firstly, a gases flow manifold part 40 is shown in FIG. 8 which is designed for either left or right hand orientation and provides a symmetrical flow to a pair of nasal cannula assembly prongs 41, 42 (see FIG. 10 or 11).

Next, a pair of soft nasal prongs 41 or 42 are provided that are capable of being attached to the top of the gases flow manifold part 40 allowing for a large range of different shaped and spaced prongs to be available to the patient. Two such configurations of prongs 41, 42 are shown in FIGS. 10 and 11. The prongs 41 of FIG. 10 are narrow elongate tubular members 43, 44 of a substantially constant diameter that are fittable into a patient's nares. The prongs are integrally molded with a body 45 that is fittable with the gases flow manifold part 40 (see FIG. 8) by appropriate means, for example, friction or snap fit. The prongs 42 of FIG. 11 are tapered tubular members 46, 47 molded to a body 48. Again, this body 48 is capable of being fitted (friction, snap or other) to the gases flow manifold part of FIG. 8. These prongs are preferably made from a soft plastics material such as silicon, although other suitable materials may be used.

With the prongs being removable they are easily cleaned and could also be disinfected for second or subsequent use.

The third part to the third form of the nasal cannula assembly shown in FIGS. 8 to 11 is the face mount part 49 of FIG. 9. The face mount part 49 comprises a head strap 53 attached to a pad 50, that may be a molded or shaped substantially rigid pad, for example, made from a plastics material such as polypropylene. The pad 36 may include a breathable cloth pad on its surface that abuts a patient's face, similar to that pad 36 described in relation to FIG. 7, or the head straps 53 may extend to sit behind the pad. The head strap 53 is preferably made from a flexible material, such as neoprene.

The plastic pad 50 is shown in FIG. 9 and has a plurality of apertures 61 formed into to allow for heat and moisture to dissipate from the patient's facial surface. The pad 50 has fastening means 51, 52 for holding the gases flow manifold part 49 in the correct position on the upper lip of the patient. The fastening means may be clips 51, 52 that are fittable into complimentary recesses 54, 55, 56, 57 provided in or on the manifold part 40 (see FIG. 8), but other appropriate fastening means may be provided with the cannula. An example of other fastening means is a loop that is integrally molded as part of the prongs which wraps around the face mount part and latches over a protrusion on the manifold part thus encapsulating the face mount part and holding the assembly together stably and securely. Another example of a fastening means is a plastic Velcro™ type attachment where one side would attach to one side of the manifold part 40 and the other side to the plastic pad 50. For the fastening means shown in FIGS. 8 and 9 at least one recess must be provided on either side of the manifold 40. In the preferred form of the nasal cannula assembly two recesses 54, 55 are provided on one side of the manifold 40 and two other recesses 56, 57 on the other side of the manifold 40.

The attachment between the face mount part 49 and the manifold part 40 allows for either left or right hand orientation of the manifold part and associated tubing.

It is envisaged the cannula of the present invention will be reusable for several wearings on a single patient and as such the nasal cannula assembly must be hygienic. It is envisaged that all the embodiments of the nasal cannula assembly of the present invention as herein described can be disassembled so that the cannula is easier to clean. The prongs and integrally attached parts are capable of being stored in a sterile solution until reused, much like false teeth are currently stored while not in use.

With a single flow entry cannula there will be less condensate due to the reduction in surface area for heat loss and thus the cannula of the present invention reduces the effects of condensation building in the tubing and cannula.

The detachable nasal cannula assembly described in relation to FIGS. 8 to 11 allows a patient on long-term therapy to order their particular prong size but maintain a common tubing connection system right to the point of connection into the manifold under the nose.

In other forms of the nasal cannula assembly of the present invention the assembly may only be provided with one nasal prong fittable into only one of the patient's nares. The purpose of such an assembly with one prong is to allow for consecutive use of a nasogastric tube. Nasogastric tubes are generally inserted in one of a patient's nares and extend down into their stomach. For example, it may be necessary or ideal for a patient to be fed by way of a nasogastric tube and to also receive heated humidified gases. The nasal cannula assembly of the present invention having only one prong would allow this.

Flexible Extension Dry Tube

Figure 12:
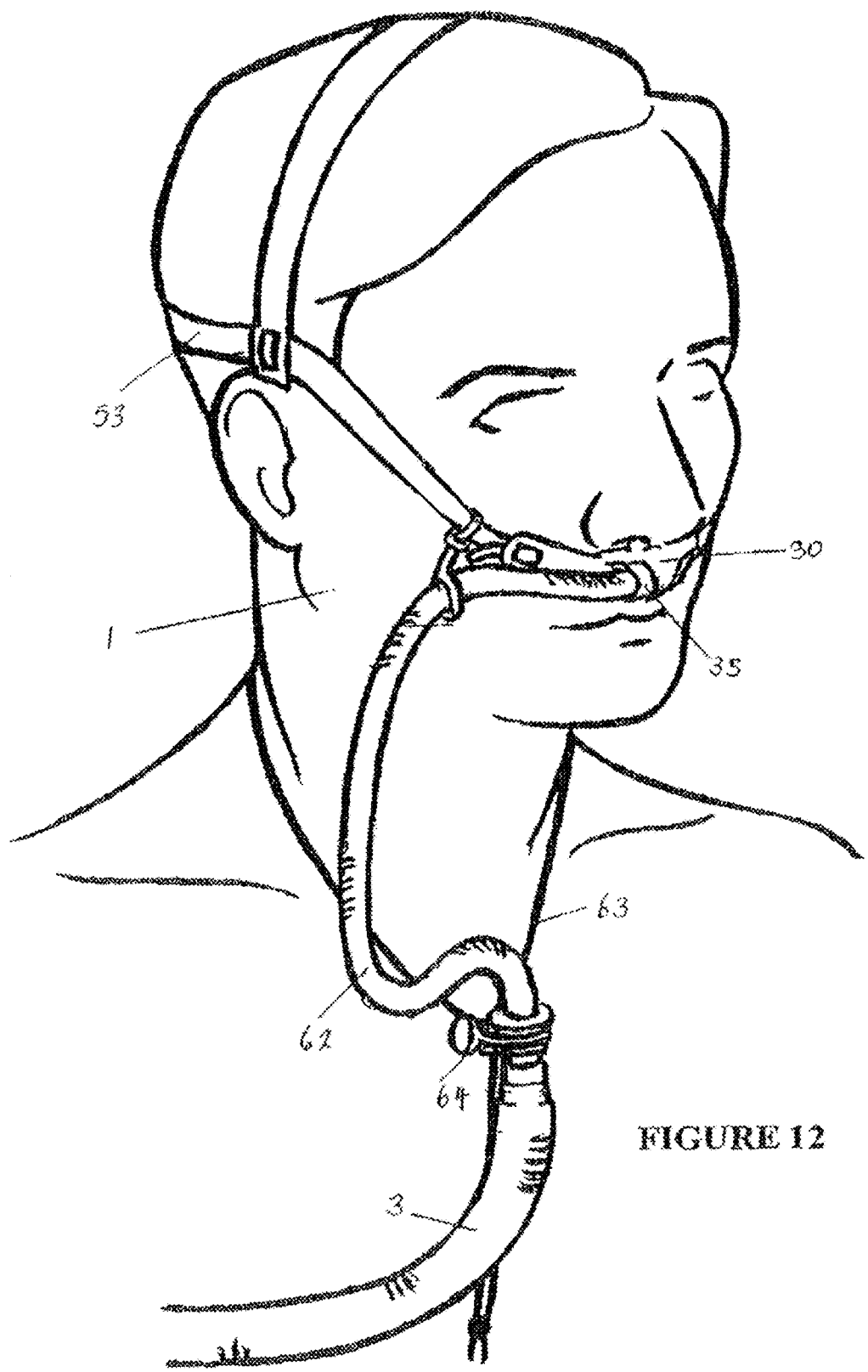
FIG. 12 is a perspective view of a patient wearing the nasal cannula assembly of FIG. 4, showing the use of a neck tie to take some weight of the tubing and a head strap assisting in the maintaining of the assembly to the patient's face.

Often an unheated flexible section of tubing is placed proximal to the patient to reduce torsion or pulling on the patient interface and reduce possible heat problems or over heating close to the patient. In order to reduce condensate forming in the unheated tubing, tubing can be provided that has vapor transmission properties. Referring now to FIG. 12 the nasal cannula of the present invention (in particular, that of the second form described herein) may be provided with a short piece of breathable tubing 62 between the nasal cannula 30 and heated tubing 3. The tubing 62 is preferably made from a material that allows for transmission of water, such as a hydrophilic material, for example SYMPATEX™.

Test results show the performance of a 420 mm length of breathable tube, operating with air input at an absolute humidity of 42.2 mg/L, an airflow of 10 liters per minute, in a room with ambient air at 22 degrees C. and 50% RH, only lowered the air temperature to 37 and the absolute humidity to 41.15 mg/L at the exit of the dry tube. In comparison a 420 mm length of non-breathable but insulated polyethylene tube under exactly the same conditions also output air at 41.15 mg/L. In the breathable tube there was significantly less condensate measured, therefore, some of the humidity that would otherwise be lost as condensate on the wall is being transmitted through the breathable wall.

The result of providing the short section of breathable tubing 62 is that a majority of humidity in the gases is transported to the patient, and there is an insignificant and immeasurable loss of humidity through the breathable wall of the short tube 62, while condensate is reduced. The design of the high airflow high humidity system has been optimized to deliver a breathable gas treatment to patients at temperatures approximating body temperature and fully saturated with water vapor for long treatment periods. The use of an unheated breathable conduit proximal to the patient to provide a connection that is highly flexible and avoids condensation by breathing would be expected to lower the humidity of the gas treatment thereby decreasing the efficacy of the treatment. These results are surprising and are counterintuitive and go some way to explaining why the use of a breathable tube as a short section of tubing before the patient has been overlooked. This short tube 62 is envisaged to be used with any tube delivering heated and humidified gases to a patient.

Neck Tie

A neck tie or lanyard may be provided with the nasal cannula assembly of the present invention. FIG. 12 shows such a tie 63. The tie 63 is preferably connected to the tubing 3 or connection 67 between the tubing 3 and breathable tube 62. A toggle 64 is preferably provided with the neck tie 63 in order to adjust the neck tie's length. The neck tie has the purpose of taking some of the weight of the tubing 3 and prevents the weight of the tubing 3 pulling on the nasal cannula assembly 30. This helps to prevent the prongs interfering with the very sensitive lining of the nasal passages. The loose fitting neck tie also provides a convenient way of connecting the tubing 3 to the patient outside the blankets. This allows the patient to turn in the bed and avoids the tubing 3 overheating if placed under the blankets.

The tie or lanyard described may be used with any breathing apparatus that supplies gases to a patient; for example it may be used with a nasal or face mask or with a tracheotomy fitting or connector. When the tie or lanyard is used with such apparatus it takes the weight of the conduit(s) or tubing supplying gases to the mask, connector or cannulae and helps reduce the pull on the mask, connector or cannulae.

Figure 16:
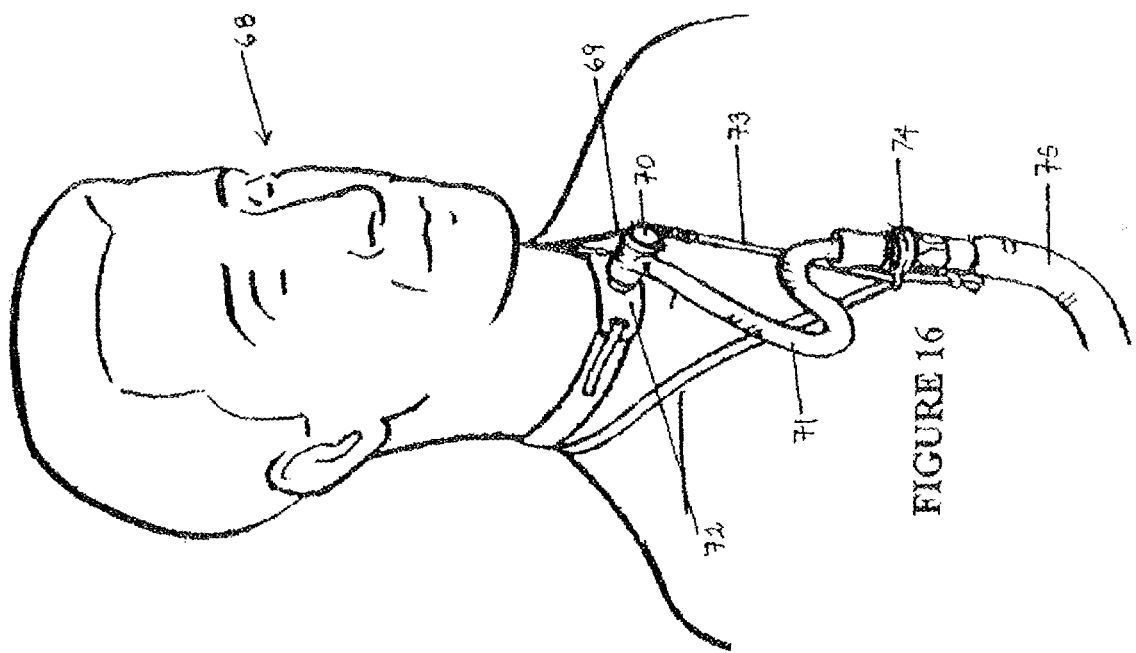
FIG. 16 is a front view of a patient with a tracheotomy and fitting attached to a breathing supply where a neck tie or lanyard is used to support the conduit supplying gases to the patient.
Figure 15:
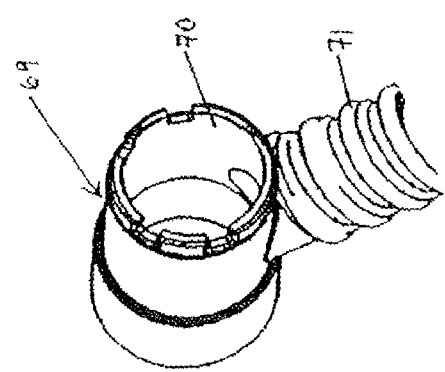
FIG. 15 is a perspective view of a tracheotomy fitting.

FIGS. 15 and 16 show a tracheotomy fitting or connector that may utilize a neck tie or lanyard of the present invention. The tracheotomy connector 69 attaches to a tracheotomy mount 72 that extends into a tracheotomy tube (not shown) through hole in a patient's 68 neck and into their airway passages. The connector 69 provides a direct coupling of a tracheotomy tube to the breathing supply of gases received through a conduit 71. Preferably the conduit 71 is constructed in a breathable material, similar to that described above, but may be a heated tube.

The connector 69 has the conduit 71 attached directly to it and also includes an expiratory port 70 to allow for expiration of gases. On inspiration no gases flow occurs out the port 70 due to the flow of gases to the connector 69 being greater than a patient's peak inspiratory flow. Therefore, there is also no or very little entraining of gases from the ambient air.

Excess weight on the tracheotomy tube may cause excess movement of the tube, with the risk of complications such as displacement or recannulation of the tracheotomy, the formation of granulation tissue or more seriously, stomal erosion. To obviate or reduce these problems a tie or lanyard 73 can be connected to the conduit 71 or additional connector 74 (that may for example connector the conduit 71 to an additional conduit 75 that supplies gases). The tie or lanyard 73 transfers the weight of the conduits 71, 75 and connector 74 from the tracheotomy tube or mount 72 and distributes it onto the neck of the patient leaving a minimal load directly on the tracheotomy tube or mount 72. Preferably the tie or lanyard 73 is adjustable so that the tie or lanyard length can be altered to suit a patient's requirements.

Ear Loops

Orientation of a nasal cannula is an essential requirement to patient comfort. If the nasal cannular is not held firmly in position, it can skew, placing unwanted load on the inside surfaces of the patient's nares. However, to overcome this head gear is often provided with nasal cannula, although, if the head gear is not tight the nasal cannula can still move. This type of tight tension can then compromise patient comfort with pressure on the head and face, while forcing the cannula further up the patient's nose. Ideally nasal cannula should attach to the patient's face in a rigid manner, yet with low loading on the head and face.

Figure 14:
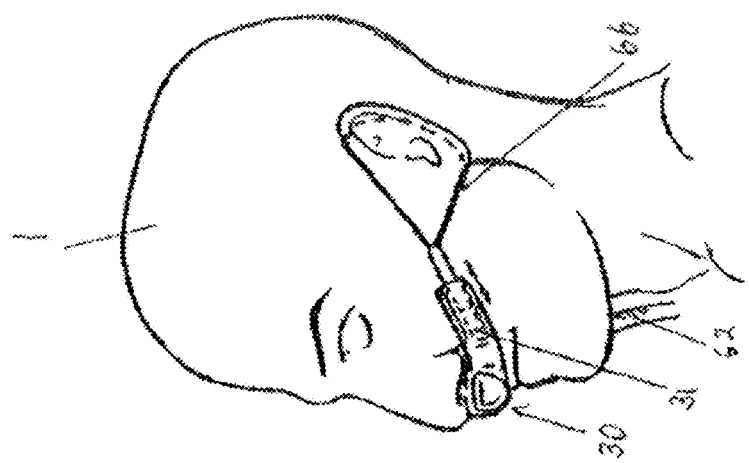
FIG. 14 is a side view of the patient and nasal cannula assembly of FIG. 13.
Figure 13:
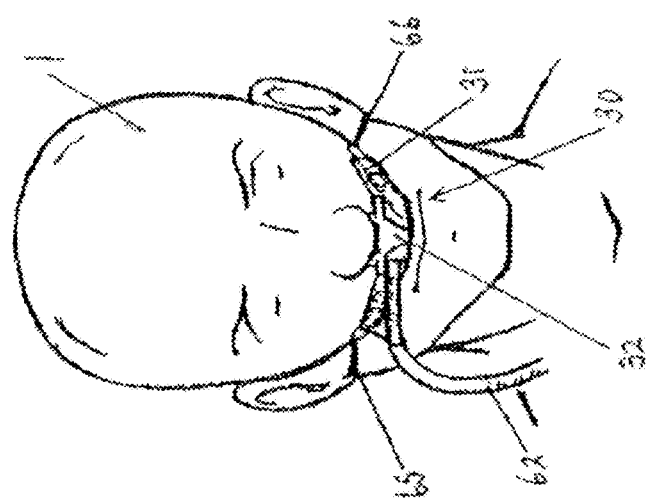
FIG. 13 is a front view of a patient wearing a nasal cannula assembly present invention where the assembly is held to the patient's face with the assistance of ear loops.

Referring to FIGS. 13 and 14 nasal cannula attachment means may be provided to hold the nasal cannula assembly 30 to the patient's face. The attachment means are preferably ear loops 65, 66 that are connected to the straps 31 of the face mount part 32 of the nasal cannula assembly 30.

The loops 65, 66 extend from the face mount part 32 around the patient's ears, and provide rigid anchoring when an inelastic material is used. The loops 65, 66 are preferably made from a thin, round cord with the ends captured in plastic, and are preferably adjustable. The plastic ends of the loops 65, 66 are inserted into purpose made cavities in the straps 31, enabling adjustment of length for a comfortable, yet firm fit.

In use, to fit the nasal cannula assembly, a first loop (for example, loop 65) is placed over one ear, the nasal cannula assembly positioned on the patient's face and in their nose, then the other ear is passed through the second loop (for example, loop 66), so both loops sit snugly behind the ears. This method of fitting the nasal cannula avoids the initial discomfort of gases being blown into the patient's eyes when the cannula assembly is pulled down the face for fitting with other headgear. Fastening the nasal cannula in this method provides an attachment means that is horizontally secure with minimum tension applied to the ear connection loops. The ear loops have the added advantage for a patient lying on their back that there are no straps behind the back of the head that are moved by head movement on the pillow.

What is claimed is:

1. A nasal cannula assembly comprising:
   a face mount portion comprising a pair of tubular nasal prongs; and
   a gases manifold portion that is attached to a tubing,
   wherein the gases manifold portion has a substantially circular inlet on a first end,
   wherein the gases manifold portion curves from the inlet on the first end around to an elongated outlet at a second end, and
   wherein the face mount portion has a recess for receiving the elongated outlet of the gases manifold portion.

2. The nasal cannula assembly of claim 1, wherein the face mount portion is integrally molded or removably attached to the face mount portion.

3. The nasal cannula assembly of claim 1, wherein the elongated outlet is an oval.

4. The nasal cannula assembly of claim 1, wherein the recess of the face mount portion is oval.

5. The nasal cannula assembly of claim 1, wherein the face mount portion is contoured such that the pressure distribution within the face mount portion is configured to force even airflow up the pair of tubular nasal prongs.

6. The nasal cannula assembly of claim 1, wherein the gases manifold is curved to direct the tubing away from a patient's face or towards a side of the patient's face.

7. The nasal cannula assembly of claim 1, wherein the elongated outlet includes at least one flange that extends from a portion of the elongated outlet and is configured to engage the gases manifold portion with the face mount portion.

8. The nasal cannula assembly of claim 1, wherein the face mount portion comprises a first strap extending from a first end of the face mount portion and a second strap extending from a second end of the face mount portion.

9. The nasal cannula assembly of claim 8 further comprising a head strap connected to the first strap and the second strap.

10. The nasal cannula assembly of claim 1 further comprising a tie or lanyard.

11. The nasal cannula assembly of claim 1, wherein the pair of tubular nasal prongs are non-sealing.

12. The nasal cannula assembly of claim 1, wherein the pair of tubular nasal prongs are shaped to fit the contours of a patient's nares.

13. A nasal cannula assembly comprising:
    a face mount portion comprising a pair of tubular nasal prongs;
    a pair of lateral extensions configured to extend laterally from the sides of the face mount portion;
    a gases manifold portion that is attached to a tubing,
    wherein the gases manifold portion curves from an inlet around to an elongated outlet, and
    wherein the face mount portion has a recess for receiving the elongated outlet of the gases manifold portion;
    a headgear coupled to the pair of lateral extensions, the headgear configured to engage a head of the patient and to at least partially support the face mount portion; and
    a support assembly connected to the tubing and configured to support at least a portion of the tubing.

14. The nasal cannula assembly of claim 13, wherein the face mount portion is integrally molded or removably attached to the face mount portion.

15. The nasal cannula assembly of claim 13, wherein the support assembly comprises a coupler configured to couple the tubing to a portion of the nasal cannula assembly along one side of a patient's face.

16. The nasal cannula assembly of claim 13, wherein the support assembly comprises a coupler configured to couple the tubing to a portion of the headgear.

17. The nasal cannula assembly of claim 13, wherein the support assembly is separate from the headgear.

18. The nasal cannula assembly of claim 13, wherein the support assembly is located proximal to a patient's neck during use.

19. The nasal cannula assembly of claim 13 further comprising a tie or lanyard.

20. The nasal cannula assembly of claim 13, wherein the gases manifold is curved to direct the tubing away from a patient's face or towards a side of the patient's face.

21. The nasal cannula assembly of claim 13, wherein the pair of tubular nasal prongs are shaped to fit the contours of a patient's nares.

22. The nasal cannula assembly of claim 13, wherein the headgear comprises flexible straps.

\* \* \* \* \*